US012629353B2

(12) United States Patent
Feng et al.

(10) Patent No.: US 12,629,353 B2
(45) Date of Patent: May 19, 2026

(54) USE OF COMPOSITION IN TREATMENT OF CEREBRAL STROKE

(71) Applicants: SIMCERE PHARMACEUTICAL CO., LTD., Jiangsu (CN); JIANGSU SIMCERE PHARMACEUTICAL CO., LTD., Jiangsu (CN)

(72) Inventors: Xiaofei Feng, Jiangsu (CN); Shunwei Zhu, Shanghai (CN); Cuncun Liu, Jiangsu (CN); Feng Wang, Jiangsu (CN); Jinsheng Ren, Jiangsu (CN)

(73) Assignees: SIMCERE PHARMACEUTICAL CO., LTD., Jiangsu (CN); JIANGSU SIMCERE PHARMACEUTICAL CO., LTD, Jiangsu (CN)

( * ) Notice: Subject to any disclaimer, the term of this patent is extended or adjusted under 35 U.S.C. 154(b) by 576 days.

(21) Appl. No.: 18/011,646

(22) PCT Filed: Jul. 7, 2021

(86) PCT No.: PCT/CN2021/104933

§ 371 (c)(1),
(2) Date: Dec. 20, 2022

(87) PCT Pub. No.: WO2022/007832

PCT Pub. Date: Jan. 13, 2022

(65) Prior Publication Data

US 2024/0033247 A1 Feb. 1, 2024

(30) Foreign Application Priority Data

Jul. 8, 2020 (CN) ......................... 202010653987.2

(51) Int. Cl.

*A61K 31/4152* (2006.01)
*A61K 9/00* (2006.01)
*A61K 31/045* (2006.01)
*A61K 47/02* (2006.01)
*A61K 47/10* (2017.01)
*A61P 9/10* (2006.01)

(52) U.S. Cl.

CPC ........ *A61K 31/4152* (2013.01); *A61K 9/0019* (2013.01); *A61K 31/045* (2013.01); *A61K 47/02* (2013.01); *A61K 47/10* (2013.01); *A61P 9/10* (2018.01)

(58) Field of Classification Search

CPC .................................................... A61K 9/0019
See application file for complete search history.

(56) References Cited

U.S. PATENT DOCUMENTS 8,658,684 B2 * 2/2014 Yin .......................... A61P 9/00 514/404
2011/0003873 A1 1/2011 Yin et al.
2017/0239335 A1 * 8/2017 Sonavaria .......... A61K 38/2257

FOREIGN PATENT DOCUMENTS

CN 101524352 A 9/2009
CN 102579432 A 7/2012
CN 105267212 A 1/2016
CN 106580966 A 4/2017
CN 106668004 A 5/2017
CN 106727287 A 5/2017
JP 2011-513249 A 4/2011

OTHER PUBLICATIONS

Kikuchi, Int. J. Mol. Sci. 2013, 14, 13909-1393.*
Xu, Stroke and Vascular Neurology 2019;4, 109-114.*
Dwivedi, Evergreening: A deceptive device in patent rights, Technology in Society 32 (2010) 324-330.*
Feldman, Understanding 'Evergreening': Making Minor Modifications Of Existing Medications To Extend Protections, Health Affairs Jun. 2022 41:6, 801-804.*
Li, Progress in Borneol Intervention for Ischemic Stroke. Front. Pharmacol. Sec. Ethnopharmacology vol. 12—2021, 1-23.*
Xu, Edaravone Dexborneol Versus Edaravone Alone for the Treatment of Acute Ischemic Stroke, Stroke. 2021;52:772-780.*
Wu, European Journal of Pharmacology 740 (2014), pp. 522-531.*
Li, American Journal of Chinese Medicine (2008), 36(4), 719-727.*
Alter, Stroke, 25(8), 1605-1610 (1994).*
Yantai Yene Pharma, ClinicalTrials.gov ID NCT03495206: Safety, Tolerability and Pharmacokinetics of Y-2(Edaravone And Borneol) Sublingual Tablet Available on the web. Not included with this action.*
Office Action (Notice of First Examination Opinion) issued Jul. 18, 2024, by the State Intellectual Property Office of People's Republic of China in corresponding Chinese Patent Application No. 202180048433.2 and an English translation of the Office Action. (12 pages).
Chen et al., Research progress of borneol promoting drug transboundary of blood-brain barrier, Chinese Traditional Patent Medicine, Sep. 2019, vol. 41 No. 9, pp. 2170-2173. (with English Abstract).
Xu et al., Edaravone Dexborneol Versus Edaravone Alone for the Treatment of Acute Ischemic Stroke, A Phase III, Randomized, Double-Blind, Comparative Trial, Stroke 2021:52, pp. 772-780, Mar. 2021.
Xu et al., Safety and efficacy of Edaravone Dexborneol versus edaravone for patients with acute ischaemic stroke: a phase II, multicentre, randomised, double-blind, multiple-dose, active-controlled clinical trial, Stroke and Vascular Neurology 2019; pp. 109-114.
Wu et al., The synergetic effect of edaravone and borneol in the rat model of ischemic stroke, European Journal of Pharmacology 740 (2014), pp. 522-531.
International Search Report and Written Opinion issued in PCT/CN2021/104933, mailed Oct. 12, 2021, with partial translation, 16 pages.
Han, The association between baseline blood pressure and short-term outcome in patients with acute ischemic stroke, Soochow University, (Sep. 2019), with English translation, 187 pages.

(Continued)

*Primary Examiner* — Nizal S Chandrakumar
(74) *Attorney, Agent, or Firm* — Buchanan Ingersoll & Rooney P.C

(57) ABSTRACT

Use of a composition in preparation of a drug for treating a patient suffering from a cerebral stroke. The composition includes edaravone and dexborneol, and the patient has a history of hypertension.

8 Claims, No Drawings

(56) References Cited

OTHER PUBLICATIONS

Abe, "5. Advances in Acute and Chronic Treatment of Cerebral Infarction", Journal of the Japanese Society of Internal Medicine, (Mar. 10, 2011), vol. 100, No. 3, pp. 717-722 and an English translation. (17 pages).
Shinohara, "Guidelines for Stroke Therapy—Overview and Problems for Physicians", Journal of the Japanese Society of Internal Medicine, (Nov. 10, 2004), vol. 93, No. 11, pp. 2449-2455 and an English translation. (20 pages).
Suzuki, "18. Cerebral Ischemia from the Viewpoint of Risk Factors", Journal of the Japanese Society of Internal Medicine, (Sep. 10, 2008), vol. 97, No. 9, pp. 2334-2340 and an English translation. (20 pages).
Office Action (Notice of Reasons for Refusal) issued Jun. 17, 2025, by the Japan Patent Office in corresponding Japanese Patent Application No. 2022-578863 and an English translation of the Office Action. (8 pages).

* cited by examiner

USE OF COMPOSITION IN TREATMENT OF CEREBRAL STROKE

CROSS REFERENCE TO RELATED APPLICATIONS

This application is a U.S. National Phase Application of PCT International Application No. PCT/CN2021/104933, filed Jul. 7, 2021, which claims benefit of priority from Chinese Patent Application No. 202010653987.2, filed Jul. 8, 2020. The contents of these applications are incorporated herein by reference.

TECHNICAL FIELD

The present invention relates to the use of a composition. More particularly, the present invention relates to the use of a composition in preparation of a drug for treating a patient suffering from a cerebral stroke.

BACKGROUND ART

In the past 15 years, cerebral stroke has been a cause of death as well as serious and long-term neurological diseases ranking second worldwide and first in China. There are many risk factors for cerebral stroke, and the common ones mainly include blood pressure, blood glucose, cholesterol levels, body mass index, smoking, physical activities, and diet, all of which are strongly associated with cerebral stroke. Therefore, stroke patients with a history of underlying diseases may have higher morbidity, mortality, recurrence, and disability rates. Although a large number of drugs are clinically available for stroke treatment, drugs actually identified for treatment of the acute and subacute phases of cerebral ischemia do not completely satisfy the needs for clinical application, especially for ischemic stroke patients with multiple diseases or a history of multiple diseases (e.g., history of hypertension, hyperlipidemia, diabetes mellitus, heart disease, etc.).

SUMMARY OF THE INVENTION

To solve the above-mentioned problems, the present invention provides a method of treating cerebral stroke in a patient with a history of hypertension.

The present invention relates to the use of a composition in preparation of a drug for treating a patient suffering from a cerebral stroke, characterized in that the composition comprises edaravone (3-methyl-1-phenyl-2-pyrazolin-5-one) and dexborneol, and the patient has a history of hypertension.

The present invention relates to the use of a composition in treatment of cerebral stroke in a patient, characterized in that the composition comprises edaravone and dexborneol, and the patient has a history of hypertension.

The present invention relates to a composition for treating cerebral stroke in a patient, characterized in that the composition comprises edaravone and dexborneol, and the patient has a history of hypertension.

The present invention relates to a method of treating cerebral stroke in a patient, the method comprising administering to a patient a therapeutically effective amount of the composition, characterized in that the composition comprises edaravone and dexborneol, and the patient has a history of hypertension.

In some embodiments, the weight ratio of edaravone to dexborneol in the composition is 1:1 to 8:1, 1:1 to 7:1, 1:1 to 6:1, 1:1 to 5:1, 1:1 to 4:1, 1:1 to 3:1, 1:1 to 2:1 or 1:1 to 1.5.

In some embodiments, the weight ratio of edaravone to dexborneol in the composition is 1:1 to 5:1.

In some embodiments, the weight ratio of edaravone to dexborneol in the composition is 1:1 to 4:1.

In some embodiments, the weight ratio of edaravone to dexborneol in the composition is 4:1.

In some embodiments, upon administration of the composition to a patient in need thereof, the plasma exposure ratio of edaravone to dexborneol in the patient is 1:1 to 8:1, 1:1 to 7:1, 1:1 to 6:1, 1:1 to 5:1, 1:1 to 4:1, 1:1 to 3:1, 1:1 to 2:1 or 1:1 to 1.5:1, preferably 1:1 to 5:1, more preferably 4:1.

In some embodiments, the composition is administered 1-3 times a day for 3-21 consecutive days.

In some embodiments, the composition is administered once every 12 hours, twice a day for 14 consecutive days.

In some embodiments, the dosage of administration of edaravone in the composition is 10-30 mg/dose.

In some embodiments, the dosage of administration of edaravone in the composition is 10 mg/dose.

In some embodiments, the dosage of administration of edaravone in the composition is 20 mg/dose.

In some embodiments, the dosage of administration of edaravone in the composition is 30 mg/dose.

In some embodiments, the composition also comprises a pharmaceutically acceptable adjuvant.

In some embodiments, the pharmaceutically acceptable adjuvant is selected from one or more of an antioxidant, a co-solvent or a solvent.

In some embodiments, the pharmaceutically acceptable adjuvant is selected from an antioxidant, a co-solvent or a solvent.

In some embodiments, the antioxidant is sodium metabisulfite.

In some embodiments, the co-solvent is propylene glycol.

In some embodiments, the solvent is water for injection.

In some embodiments, the cerebral stroke is ischemic stroke.

In some embodiments, the cerebral stroke is acute ischemic stroke.

Beneficial effects of the present invention: we surprisingly found that the composition comprising edaravone and dexborneol of the present invention has achieved a significant curative effect on stroke patients with a history of hypertension, and the present invention provides a more effective therapeutic agent and treatment regimen for patients having acute ischemic stroke with hypertension.

DETAILED DESCRIPTION OF EMBODIMENTS

The technical solutions of the present invention will be described in detail by the following examples, but the scope of protection of the present invention includes but is not limited thereto.

EXAMPLES

The methods and data of the examples of the present invention are derived from clinical trials, and the objectives, methods and results of the trials are provided as follows.

Trial Objective: To Study the Efficacy of Edaravone and Dexborneol Solution for Injection in the Subgroup of Stroke Patients with a History of Underlying Diseases A multicenter, randomized, double-blind, positive drug (edaravone solution for injection) controlled phase III clinical trial was conducted. A total of 1200 acute ischemic stroke patients with the onset of ≤48 h were enrolled and randomly assigned to either the edaravone and dexborneol solution for injection group or the edaravone group in a ratio of about 1:1 for pharmacodynamic and safety studies. The efficacy of edaravone and dexborneol solution for injection for the treatment of acute ischemic stroke patients with a history of underlying diseases was studied and analyzed. The 1200 stroke patients enrolled were included into subgroups according to the diagnostic criteria described below. Patients in each subgroup were randomly assigned to receive either edaravone and dexborneol solution for injection or edaravone solution for injection in a ratio of about 1:1, with a treatment duration of 14 consecutive days and follow-up to day 90.

Inclusion Criteria for Subjects:

The main criteria for subject inclusion were: aged 35-80; male or female; diagnosed with ischemic stroke (cerebral infarction) according to the "Diagnostic Points for Various Types of Cerebrovascular Diseases" published by the Fourth National Cerebrovascular Disease Conference; clear localizing neurological signs; and neurological deficit score: 4≤NIHSS≤24, and the sum of the fifth (motor arm) and sixth (motor leg) items in the NIHSS of ≥2; subjects who had received the treatment of intravenous thrombolysis, arterial thrombolysis and neuroprotective agents were excluded.

Subjects enrolled above were considered to have a history of hypertension if one of the following conditions was met: prior to or during the enrollment, systolic blood pressure (SBP) of ≥140 mmHg (1 mmHg=0.133 kPa) and/or diastolic blood pressure (DBP) of ≥90 mmHg according to office blood pressure measured 3 times on different days, without taking antihypertensive drugs. SBP of ≥140 mmHg and DBP of <90 mmHg; or subjects with systolic and diastolic blood pressure below 140 mmHg and 90 mmHg, respectively, but currently taking antihypertensive drugs.

Subjects enrolled above were considered to have a history of hyperlipidemia if the following conditions were met: prior to or during enrollment, fasting serum total cholesterol in a subject exceeded 5.72 mmol/L and fasting serum triglyceride exceeded 1.70 mmol/L; or subjects with serum total cholesterol and serum triglyceride not exceeding the criteria above (total cholesterol of no more than 5.72 mmol/L and triglyceride of no more than 1.70 mmol/L), but currently taking lipid-lowering drugs; and those who met the diagnostic criteria of the Chinese Guidelines for the Prevention and Treatment of Dyslipidemia in Adults (Revised 2016).

Specifications and Sources of Drugs:

1) Name of the investigational drug: edaravone and dexborneol solution for injection;

Specification: 5 mL: 12.5 mg (edaravone 10 mg, (+)-2-borneol 2.5 mg), the ingredients as adjuvants: sodium metabisulfite, propylene glycol and water for injection; the structure of dexborneol is

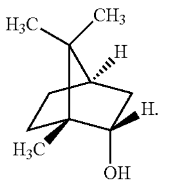

Storage conditions: Protected from light, keep sealed and stored in a cool place (not exceeding 20° C.);

Manufacturer: Nanjing Simcere Dongyuan Pharmaceutical Co., Ltd.

2) Name of the positive control drug: edaravone solution for injection;

Specification: 5 mL: 10 mg (edaravone 10 mg);

Storage conditions: Protected from light, keep sealed and stored in a cool place (not exceeding 20° C.);

Manufacturer: Nanjing Simcere Dongyuan Pharmaceutical Co., Ltd.

The investigational drug and the positive control drug were completely identical in color and shape, and to ensure blinding, the drug packaging and lot numbers were completely identical in both groups, and the packaging lot numbers were uniformly labeled. Each subject randomized into the groups was assigned 1 large medicine box comprising 14 small boxes for a medication course of 14 days, 1 small box per day. Each small box contained 6 vials of drug and 3 vials of drugs in 1 small box were used each time. The drugs were administered once every 12 h, twice a day. The specific drug packaging specifications and quantities are shown in the table below:

| Groups of the trial | Number of small boxes | Drug composition per small box |
|---|---|---|
| Edaravone and dexborneol solution for injection group | 14 | 6 vials |
| Edaravone control group | 14 | 6 vials |

Trial Method:

Subjects were randomly assigned to groups. Subjects in the test group received 37.5 mg of edaravone and dexborneol solution for injection by intravenous injection, twice daily for 14 consecutive days; and subjects in the control group received 30 mg of edaravone solution for injection by intravenous injection, twice daily for 14 consecutive days. No dose adjustment was allowed during the study, and the cumulative delay in the administration time cannot exceed 2 days. Use of neuroprotective agents and thrombolytic drugs listed in the Chinese Guidelines for the Diagnosis and Treatment of Acute Ischemic Stroke (2010 edition) was prohibited during the study.

More Specifically, the Dosing Regimens for Both Groups in the Present Clinical Trial were as Follows:

Edaravone and dexborneol solution for injection group: prior to administration, 3 vials of drugs in 1 small box were added into 100 mL of 0.9% sodium chloride injection for dilution and then administered by intravenous drip over 30 minutes, once every 12 hours, twice a day for 14 consecutive days.

Edaravone group: The administration method was identical to that of the test drug, i.e., edaravone and dexborneol solution for injection. Prior to administration, 3 vials of drugs in 1 small box were added into 100 mL of 0.9% sodium chloride injection for dilution and then administered by intravenous drip over 30 minutes, once every 12 hours, twice a day for 14 consecutive days.

Evaluation Indicators:

The primary efficacy endpoint was the proportion of patients with an mRS score ≤1 on day 90 of treatment.

For the overall outcome scale rating, the Modified Rankin Scale (mRS) for the overall assessment of disability was used. The study endpoints were also the primary endpoints recommended in the "Technical Guidelines for Clinical Trials of Acute Ischemic Stroke Therapeutics" issued by the National Medical Products Administration. The mRS scale is currently the most frequently used functional outcome evaluation scale in clinical trials of cerebral stroke and the score is graded from 0 for no symptoms to 5 for severe disability, with an additional grade 6 for death added in some trials. In clinical trials, the mRS scores of 0 to 1 are generally chosen as the criterion for determining that a subject has no disability after a stroke, and some clinical trials choose the mRS scores of 0 to 2 as the determination criterion. In the present application, the mRS scores of 0-1 were chosen as the determination criterion. Results of the trial are shown in Table 1.

TABLE 1 mRS score on day 90 of treatment

| Disease history of subject patients | | Edaravone and dexborneol solution for injection | Edaravone solution for injection (control group) |
|---|---|---|---|
| With a history of hypertension | Number of subject patients | 390 | 377 |
| | Number of patients with mRS score ≤1 | 252 | 199 |
| | Percentage of patients with mRS score ≤1 | 64.6 | 52.8 |
| Without a history of hypertension | Number of subject patients | 207 | 215 |
| | Number of patients with mRS score ≤1 | 141 | 142 |
| | Percentage of patients with mRS score ≤1 | 68.1 | 66.1 |
| With a history of hyperlipidemia | Number of subject patients | 44 | 41 |
| | Number of patients with mRS score ≤1 | 24 | 22 |
| | Percentage of patients with mRS score ≤1 | 54.6 | 53.7 |

The results in Table 1 showed that the edaravone solution for injection was less therapeutically effective in stroke patients with a history of hypertension than in stroke patients without a history of hypertension, and the mRS scores on day 90 were 52.8% and 66.1%, respectively. However, the edaravone and dexborneol solution for injection can be significantly more therapeutically effective in stroke patients with a history of hypertension than edaravone solution. The efficacy of the edaravone and dexborneol solution for injection was 64.6%, which was 22% (100%*(64.6−52.8)/52.8=22%) higher than that of edaravone solution (52.8%). For stroke patients with a history of hyperlipidemia, the effect of edaravone and dexborneol solution for injection was not significantly different from that of edaravone solution for injection. The results above show that edaravone dexborneol has a good therapeutic effect on stroke patients with a history of hypertension and performs better than edaravone alone.

What is claimed is:

1. A method for treating cerebral stroke, comprising administering a composition comprising edaravone and dexborneol to a patient in need thereof, wherein the patient has a history of hypertension;

wherein, the weight ratio of edaravone to dexborneol in the composition is 4:1; the composition further comprises a pharmaceutically acceptable adjuvant, and 5 the pharmaceutically acceptable adjuvant is selected from sodium metabisulfite, propylene glycol and water for injection.

2. The method according to claim 1, wherein the composition is administered 1-3 times a day for 3-21 consecutive days.

3. The method according to claim 1, wherein the composition is administered once every 12 hours, twice a day for 14 consecutive days.

4. The method according to claim 1, wherein the dosage of administration of edaravone in the composition is 10-30 mg/dose.

5. The method according to claim 1, wherein the dosage of administration of edaravone in the composition is 10 mg/dose, 20 mg/dose or 30 mg/dose.

6. The method according to claim 1, wherein the cerebral stroke is ischemic stroke.

7. The method according to claim 1, wherein the cerebral stroke is acute ischemic stroke.

8. The method according to claim 1, wherein upon administration of the composition, the plasma exposure ratio of edaravone to dexborneol in the patient is 4:1.

* * * * *